(12) United States Patent
Amako et al.

(10) Patent No.: US 9,057,697 B2
(45) Date of Patent: Jun. 16, 2015

(54) OPTICAL DEVICE WITH PROPAGATING AND LOCALIZED SURFACE PLASMONS AND DETECTION APPARATUS

(71) Applicant: Seiko Epson Corporation, Tokyo (JP)

(72) Inventors: Jun Amako, Tsurugashima (JP); Mamoru Sugimoto, Chino (JP); Hideaki Koike, Chino (JP)

(73) Assignee: Seiko Epson Corporation (JP)

( * ) Notice: Subject to any disclaimer, the term of this patent is extended or adjusted under 35 U.S.C. 154(b) by 299 days.

(21) Appl. No.: 13/651,791

(22) Filed: Oct. 15, 2012

(65) Prior Publication Data

US 2013/0092823 A1 Apr. 18, 2013

(30) Foreign Application Priority Data

Oct. 17, 2011 (JP) .................. 2011-227746

(51) Int. Cl.
| | |
|---|---|
| *G01N 21/552* | (2014.01) |
| *G02B 27/60* | (2006.01) |
| *G01J 3/26* | (2006.01) |
| *G01J 3/12* | (2006.01) |

(52) U.S. Cl.
CPC .................. *G01N 21/554* (2013.01); *G01J 3/26* (2013.01); *G01J 3/12* (2013.01); *G02B 27/60* (2013.01)

(58) Field of Classification Search
USPC ................ 250/208.1, 208.2, 226, 216, 214.1, 250/214 R; 257/431–433
See application file for complete search history.

(56) References Cited

U.S. PATENT DOCUMENTS

| | | | |
|---|---|---|---|
| 7,079,250 B2 | 7/2006 | Mukai | |
| 7,351,588 B2 | 4/2008 | Poponin | |
| 7,399,445 B2 | 7/2008 | Kuroda et al. | |
| 7,639,355 B2 | 12/2009 | Fattal et al. | |

(Continued)

FOREIGN PATENT DOCUMENTS

| | | |
|---|---|---|
| JP | 2000-356587 | 12/2000 |
| JP | 2003-268592 | 9/2003 |

(Continued)

OTHER PUBLICATIONS

Chu, Yizhuo et al., "Experimental Study of the Interaction Between Localized and Propagating Surface Plasmons", School of Engineering and Applied Sciences, Harvard University, Cambridge, Massachusetts 02138, Optics Letters, vol. 34, No. 3, Feb. 1, 2009, pp. 244-246.

(Continued)

*Primary Examiner* — Francis M Legasse, Jr.
(74) *Attorney, Agent, or Firm* — Harness, Dickey & Pierce, P.L.C.

(57) ABSTRACT

An optical device includes a first protrusion group in which protrusions protruding from a conductor surface of a substrate are arranged in a first direction with a first period, a dielectric layer that covers the conductor surface and the first protrusion group, and a second protrusion group in which metal nanoparticles are arranged on the dielectric layer in the first direction with a second period different from the first period. When one of the first period and the second period is defined as Px1, the other of the first period and the second period is defined as Px2, and the wavelength of irradiation light is defined as $\lambda$, $\lambda > Px1 > Px2$ and $0 < Px1 - Px2 < Px1/2$ are satisfied.

13 Claims, 12 Drawing Sheets

(56) References Cited

U.S. PATENT DOCUMENTS

| | | |
|---|---|---|
| 7,733,491 B2 | 6/2010 | Kuroda et al. |
| 8,085,405 B2 | 12/2011 | Ogawa |
| 8,093,065 B2 | 1/2012 | Poponin |
| 2005/0064303 A1* | 3/2005 | Yamada et al. .............. 430/5 |
| 2008/0198376 A1 | 8/2008 | Poponin |
| 2010/0220377 A1* | 9/2010 | Yamada et al. ............ 359/241 |
| 2011/0114859 A1 | 5/2011 | Amako et al. |
| 2011/0116088 A1 | 5/2011 | Amako et al. |
| 2011/0165261 A1 | 7/2011 | Derby et al. |
| 2011/0267613 A1 | 11/2011 | Amako et al. |
| 2011/0279817 A1 | 11/2011 | Amako et al. |
| 2012/0107958 A1 | 5/2012 | Poponin |

FOREIGN PATENT DOCUMENTS

| | | |
|---|---|---|
| JP | 2003-270132 | 9/2003 |
| JP | 2007-240361 | 9/2007 |
| JP | 2007-248284 | 9/2007 |
| JP | 2007-303973 | 11/2007 |
| JP | 2011-128133 | 6/2011 |
| JP | 2011-128135 | 6/2011 |
| JP | 2011-141264 | 7/2011 |
| JP | 2011-141265 | 7/2011 |

OTHER PUBLICATIONS

Inoue, Masahiro et al., "Surface Enhanced Raman Scattering by Metal Spheres. 1. Cluster Effect", Institute of Applied Physics, University of Tsukuba, Sakura, Ibaraki 305, Department of Applied Physics, Faculty of Engineering, University of Tokyo, Journal of the Physical Society of Japan, vol. 52, No. 11, Nov. 1983, pp. 3853-3864.

* cited by examiner

DOT PATTERN

ELLIPSE PATTERN

OPTICAL DEVICE WITH PROPAGATING AND LOCALIZED SURFACE PLASMONS AND DETECTION APPARATUS

BACKGROUND

1. Technical Field

The present invention relates to an optical device and a detection apparatus.

2. Related Art

Recently, the demand for sensors used for medical diagnosis or inspection of food and drink has increased and development of a high-sensitivity and small-sized sensor has been required. In order to satisfy such requirements, various types of sensors using electrochemical techniques and the like have been studied. Among these, a sensor using surface plasmons resonance (SPR) has increasingly attracted attention from the viewpoints of possibility of integration, low cost, and usefulness for any measurement environment.

For example, JP-A-2000-356587 discloses a technique for improving the sensitivity of a sensor using localized surface plasmons resonance (LSPR).

In "Experimental Study of the Interaction between Localized and Propagating Surface Plasmons", OPTICS LETTERS/Vol. 34, No. 3/Feb. 1, 2009, a technique of improving the sensitivity of a sensor using propagating surface plasmons (PSP) and localized surface plasmons (LSP) together is disclosed.

In JP-A-2000-356587, as shown in FIG. 1, metal fine particles 20 are fixed to the surface of a transparent substrate 10 and the transparent substrate 10 is irradiated with incident light to measure the absorbance of the metal fine particles 20. As shown in FIG. 2, when a target is attached to the metal fine particles 20, the absorbance spectrum indicated by A1 is changed to the absorbance spectrum indicated by A2. In the technique described in JP-A-2000-356587, the variation in medium around the metal fine particles is detected through the use of the change in absorbance and the adsorption or deposition of the target is detected.

However, in this technique, it is difficult to form the metal fine particles to be uniform in size or shape or to regularly arrange the metal fine particles. When the size or arrangement of the metal fine particles cannot be controlled, the absorption wavelength or the resonance wavelength caused from the plasmons resonance is non-uniform. Accordingly, as shown in FIG. 2, the width of the absorbance spectrum becomes larger and the peak intensity is lowered. When the peak intensity is lowered, the variation in the signal for detecting the variation in the medium around the metal fine particles becomes smaller and the improvement in sensitivity of a sensor is limited. Accordingly, the sensitivity of a sensor is not sufficient to specify a material in an absorbance spectrum.

In a surface-enhanced Raman scattering (SERS) sensor described in JP-A-2000-356587, since only one resonance peak is used, the wavelength of the resonance peak has to match any of an excitation wavelength or a Raman scattering wavelength. In this case, only an electric field enhancement effect in the scattering process of any one is used and thus a high electric field enhancement effect cannot be expected.

On the other hand, in "Experimental Study of the Interaction between Localized and Propagating Surface Plasmons", OPTICS LETTERS/Vol. 34, No. 3/Feb. 1, 2009, as shown in FIG. 3, a sensor is disclosed in which an Au film 40 with a thickness of 100 nm is bonded onto a glass substrate 30, an SiO$_2$ layer 50 with a thickness of 20 nm is formed on the Au film 40, and plural Au discs 60 with a diameter of 100 to 170 nm are two-dimensionally arranged on the SiO$_2$ layer 50 in a period of P=780 nm.

In this sensor, the propagating surface plasmons (PSP) are excited in the interface between the Au film 40 and the SiO$_2$ layer 50 and the localized surface plasmons (LSP) is excited in the Au discs 60. Here, the PSP has a specific wave number, and this wave number is determined by the dispersion relationship in the interface between the Au film 40 and the SiO$_2$ layer 50 and the excitation wavelength. The wave number of the PSP is determined by the arrangement period P of the Au discs 60 and the real part thereof is equal to $2\pi/P$. For example, when the excitation wavelength is selected from the visible range, the arrangement period P of the Au discs 60 is 780 nm, which is relatively large.

On the other hand, the Au discs 60 are sites (referred to as hot sites) having a large local electric field and an increase in sensitivity of the sensor requires an increase in density of the hot sites. However, the arrangement period P of the Au discs 60 used to determine the wave number of the PSP is 5 to 10 times the diameter of the Au discs, which is large, and thus the density of the hot sites is markedly small. However, when the arrangement period P is selected to be small, the coupling of the LSP and the PSP is weakened and thus a large local electric field cannot be achieved. When the outer size of the Au discs 60 is made to increase while guaranteeing a large period P, the resonance wavelength is shifted to a long wavelength side (red side) and departs from the excitation wavelength, and thus a large local electric field cannot be expected.

That is, in the structure disclosed in "Experimental Study of the Interaction between Localized and Propagating Surface Plasmons", OPTICS LETTERS/Vol. 34, No. 3/Feb. 1, 2009, the hot sites having a large local electric field cannot be formed with a high density and thus a sensor having high sensitivity cannot be implemented.

SUMMARY

An advantage of some aspects of the invention is that it provides an optical device which can increase the density of metal nanoparticles serving as hot sites by using propagating surface plasmons and localized surface plasmons together and a detection apparatus using the optical device.

(1) An aspect of the invention relates to a detection apparatus including: a light source; an optical device that emits light specific to a sample by introduction of the sample and irradiation with light of a wavelength λ from the light source; and an optical detection unit that detects the light specific to the sample emitted from the optical device, wherein the optical device includes a first protrusion group in which protrusions protruding from a conductor surface of a substrate are arranged in a first direction with a first period, a dielectric layer that covers the conductor surface and the first protrusion group, and a second protrusion group in which metal nanoparticles are arranged on the dielectric layer in the first direction with a second period different from the first period, and wherein any of a combination in which the first period is Px1 and the second period is Px2 and a combination in which the first period is Px2 and the second period is Px1 satisfies λ>Px1>Px2 and 0<Px1−Px2<Px1/2.

According to the aspect of the invention, it is confirmed that the localized surface plasmons LSP excited by the second protrusion group and the propagating surface plasmons PSP are coupled to form a strong electric field having the second protrusion group as a hot site.

The reason of enhancement of the coupling of the localized surface plasmons LSP and the propagating surface plasmons PSP is presumed as follows. It is thought that moire (interference fringe) having a necessary period P is expressed by the difference between the first period and the second period. The propagating surface plasmons PSP generated in the interface between the first protrusion group and the dielectric layer are coupled to an evanescent field having a wave number of K0. The wave number K0 is determined by the moire period Px and is $2\pi/Px$. It is thought that the presence of the moire enhances the coupling of the localized surface plasmons LSP and the propagating surface plasmons PSP and thus a large enhanced electric field appears. The moire period Px in the first direction is expressed by Expression (1).

$$Px=Px1*Px2/(Px1-Px2) \quad (1)$$

On the basis of $\lambda>Px1>Px2$ and Expression (1), the following expression is obtained.

$$Px1 - Px2 = Px1 - [Px/(Px+Px1)]Px1$$
$$= Px1[1 - Px/(Px+Px1)]$$
$$= Px1[1 - 1/(1+Px1/Px)]$$

Here, since $0<Px1<Px$, Expression (2) is established.

$$0<Px1-Px2<Px1/2 \quad (2)$$

When the wave number of the propagating surface plasmons PSP is defined as K0, Expression (3) is established from Expression (1).

$$Px=2\pi/K0=Px1*Px2/(Px1-Px2) \quad (3)$$

In this way, it can be seen that the wave number of the propagating surface plasmons PSP is not determined by only the period (one of Px1 and Px2) of the second protrusion group as a hot site as described in "Experimental Study of the Interaction between Localized and Propagating Surface Plasmons", OPTICS LETTERS/Vol. 34, No. 3/Feb. 1, 2009, but is determined by the difference and the product of the first and second periods (Px1 and Px2) as expressed by Expression (3). Accordingly, the period (one of Px1 and Px2) of the second protrusion group in which the localized surface plasmons LSP are excited does not have to be set to be large as described in "Experimental Study of the Interaction between Localized and Propagating Surface Plasmons", OPTICS LETTERS/Vol. 34, No. 3/Feb. 1, 2009, but it is possible to raise the sensitivity of the optical device and the detection apparatus by raising the density of the second protrusion group as a hot site.

(2) In one aspect of the invention, the second period of the second protrusion group may be set to Px2 and the first period of the first protrusion group may be set to Px1.

When the difference between the first period and the second period is small and the second period of the second protrusion group is any of Px1 and Px2, it is possible to raise the density of the hot sites. By setting the second period of the second protrusion group to Px2 (<Px1), it is possible to further raise the density of the hot sites.

(3) In one aspect of the invention, moire with a period Px may be formed in the first direction on the basis of the difference and the product of the first period and the second period and the period Px of the moire may satisfy $\lambda>Px>Px1>Px2$.

In the aspect of the invention, even when the moire period P which is considered to determine the wave number of the propagating surface plasmons PSP is guaranteed to be, for example, 780 nm, which is relatively large, similarly to the period P of the Au discs 60 in "Experimental Study of the Interaction between Localized and Propagating Surface Plasmons", OPTICS LETTERS/Vol. 34, No. 3/Feb. 1, 2009, the density of the hot sites (the second protrusion group) is not markedly lowered.

(4) In one aspect of the invention, the first protrusion group may be a metal lattice in which the protrusions are arranged in the first direction with the first period, and the second protrusion group may be a metal nanostructure in which the metal nanoparticles are arranged in the first direction with the second period and are periodically arranged in a second direction intersecting the first direction.

According to this configuration, the metal nanoparticles serving as the hot sites are two-dimensionally arranged to form an enhanced electric field around the metal nanoparticles, thereby raising the sensitivity of a sensor.

(5) In one aspect of the invention, the first protrusion group may be a two-dimensional metal lattice in which the protrusions are arranged in the first direction with the first period and are arranged in a second direction intersecting the first direction with a third period, the second protrusion group may be a metal nanostructure in which the metal nanoparticles are arranged in the first direction with the second period and are arranged in the second direction with a fourth period, and any of a combination in which the third period is Py1 and the first period is Py2, a combination in which the third period is Py1 and the second period is Py2, a combination in which the fourth period is Py1 and the first period is Py2, and a combination in which the fourth period is Py1 and the second period is Py2 may satisfy $\lambda>Py2>Py1$ and $0<Py2-Py1<Py2/2$.

When the first and second protrusion groups are periodically arranged in the first and second directions, it is clarified that the moire period Py in the second direction satisfies $\lambda>Py>Py2>Py1$ and Expressions 1 to 3 are established in the second direction. By two-dimensionally arranging the first and second protrusion groups, circularly-polarized light can be used as irradiation light.

(6) In one aspect of the invention, the surface of the dielectric layer on which the second protrusion group is formed may be a flat surface.

That is, by setting the surface of the dielectric layer to a flat surface not reflecting the uneven pattern of the first protrusion group, it is possible to arrange the second protrusion with a predetermined period regardless of the unevenness of the first protrusion group.

(7) Another aspect of the invention relates to a detection apparatus including: a light source; an optical device that emits light specific to a sample by introduction of the sample and irradiation with light from the light source; and an optical detection unit that detects the light specific to the sample emitted from the optical device, wherein the optical device includes a first protrusion group in which protrusions protruding from a conductor surface of a substrate are arranged in a first direction with a first period, a dielectric layer that covers the conductor surface and the first protrusion group, and a second protrusion group in which metal nanoparticles are arranged on the dielectric layer in the first direction with a second period different from the first period, and wherein moire based on the first period and the second period is expressed to enhance the coupling of local surface plasmons and propagating surface plasmons PSP through the use of the moire.

As described above, it is thought that moire (interference fringe) having a necessary period P is expressed by the difference between the first period and the second period. The propagating surface plasmons generated in the interface between the first protrusion group and the dielectric layer is coupled to an evanescent field having a wave number of K0. The wave number K0 is determined by the moire period Px and is 2π/Px. It is thought that the presence of the moire enhances the coupling of the localized surface plasmons LSP and the propagating surface plasmons PSP and thus a large enhanced electric field appears.

BRIEF DESCRIPTION OF THE DRAWINGS

The invention will be described with reference to the accompanying drawings, wherein like numbers reference like elements.

DESCRIPTION OF EXEMPLARY EMBODIMENTS

Figure 1:
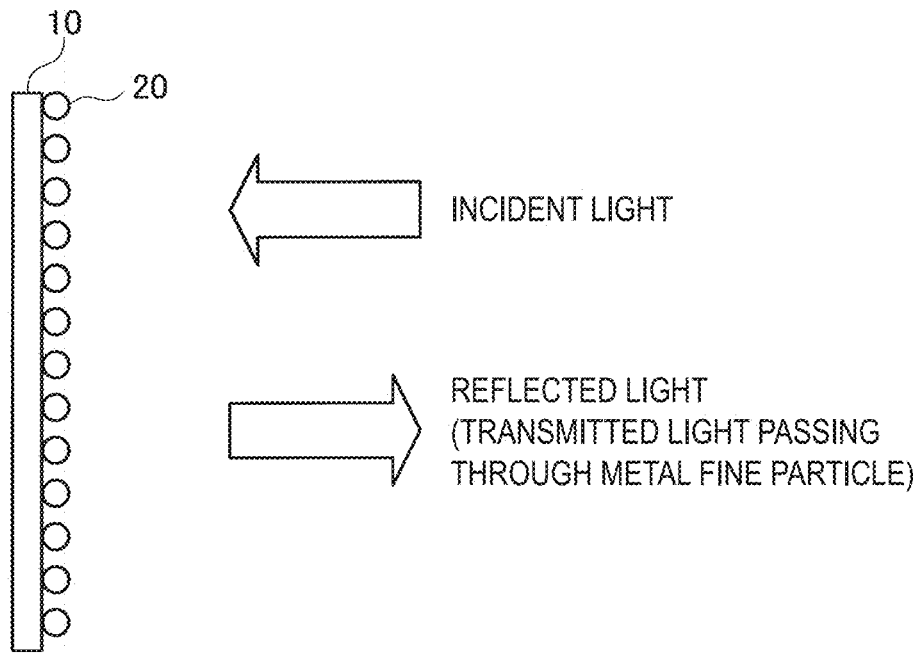
FIG. 1 is a diagram illustrating a sensor using localized surface plasmons according to the related art.
Figure 2:
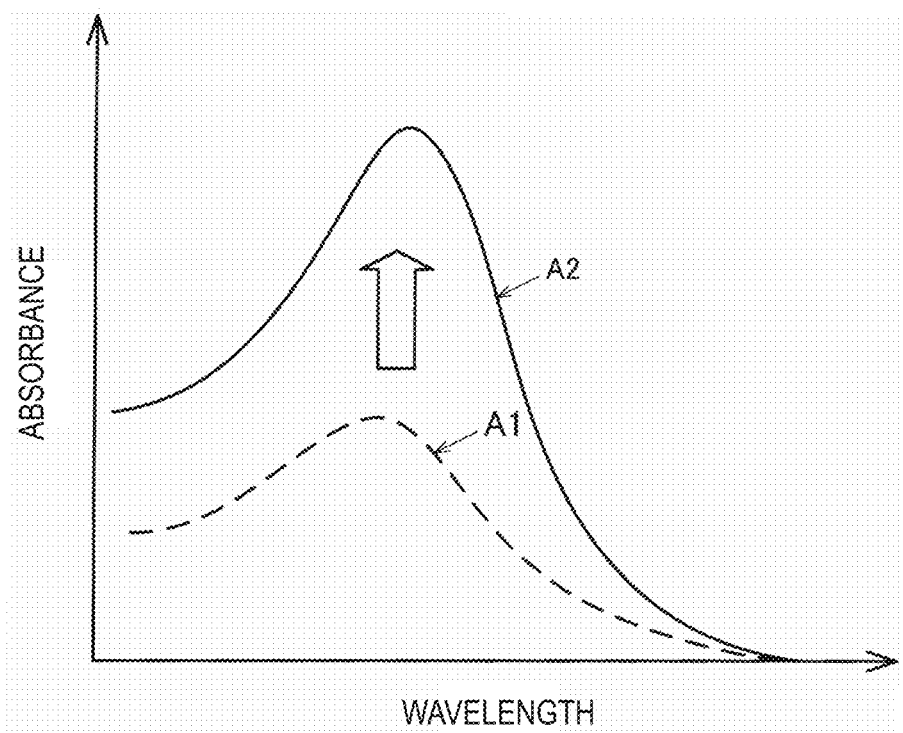
FIG. 2 is a characteristic diagram illustrating an absorbance spectrum of the sensor shown in FIG. 1.

Hereinafter, exemplary embodiments of the invention will be described in detail. The exemplary embodiments of the invention to be described below do not improperly limit the details of the invention described in the appended claims, but all the elements described in the exemplary embodiments cannot be said to be essential as resolution means of the invention. Here, constituent elements in the drawings are drawn with different scales so as to be recognizable in the drawings.

1. Principle of Detection

Figure 4A:
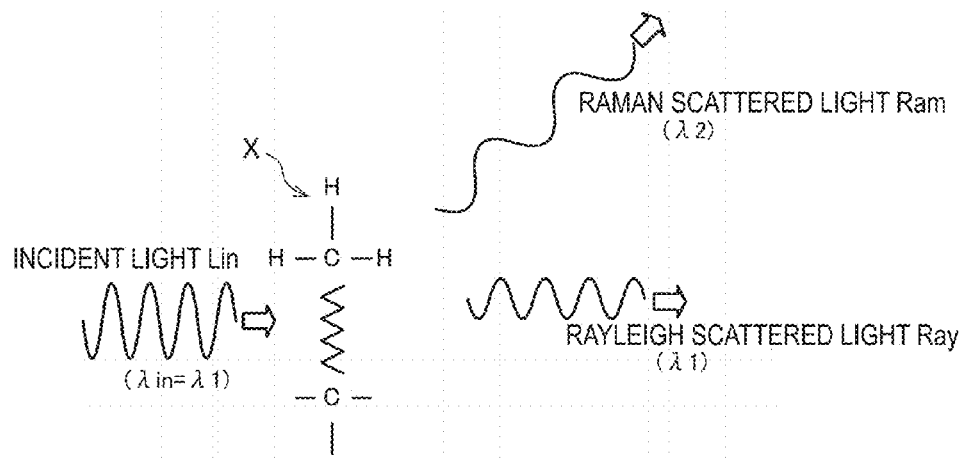
FIG. 4A is a diagram illustrating the principle of Raman scattering spectroscopy and FIG. 4B is a diagram illustrating an example of a Raman spectrum acquired through the Raman scattering spectroscopy.

FIG. 4A is a diagram illustrating the principle of Raman scattering spectroscopy. As shown in FIG. 4A, when light Lin of a single wavelength is applied to a target molecule X (target), Raman scattered light Ram of a wavelength λ2 different from the wavelength λin of the incident light Lin is present in the scattered light. The energy difference between the Raman scattered light Ram and the incident light Lin corresponds to energy of a vibrational level, a rotational level, or an electronic level of the target molecule X. Since the target molecule X has vibrational energy specific to the structure thereof, it is possible to specify the target molecule X by using the light Lin of a single wavelength.

For example, when the vibrational energy of the incident light Lin is defined as V1, the vibrational energy of the target molecule X is defined as V2, and the vibrational energy of the Raman scattered light Ram is defined as V3, V3=V1−V2 is satisfied. That is, since V3 is vibrational energy based on V2, the target molecule X can be specified by measuring the wavelength λ2 of the Raman scattered light Ram.

After colliding with the target molecules X, most of the incident light Lin has the same magnitude of energy as before the collision. This elastic scattered light is referred to as Rayleigh scattered light Ray. For example, when the vibrational energy of the Rayleigh scattered light Ray is defined as V4, V4=V1 is established. That is, the wavelength λ1 of the Rayleigh scattered light Ray is λ1=λin.

Figure 4B:
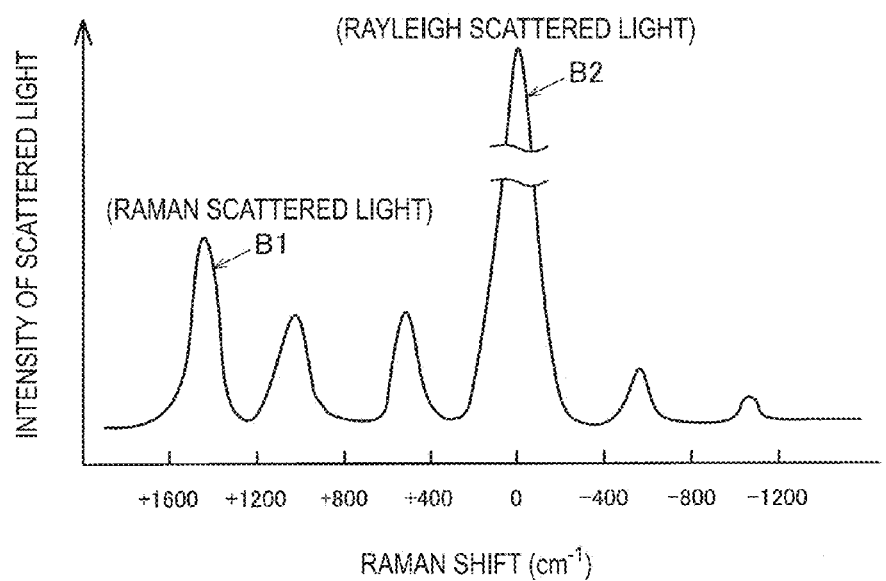

FIG. 4B shows an example of a Raman spectrum (the relationship between Raman shift and Raman scattering intensity) acquired through Raman scattering spectroscopy. The horizontal axis of the graph shown in FIG. 4B represents the Raman shift. The Raman shift means a difference between the wave number (the frequency of vibration) of the Raman scattered light Ram and the wave number of the incident light Lin and represents a value specific to the molecular coupling state of the target molecules X.

As shown in FIG. 4B, by comparing the scattering intensity (spectrum peak) of the Raman scattered light Ram indicated by B1 and the scattering intensity of the Rayleigh scattered light Ray indicated by B2 with each other, it can be seen that the Raman scattered light Ram is weaker. In this way, the Raman scattering spectroscopy is a measurement method which is excellent in identification capability of the target molecules X but is poor in sensitivity for sensing the target molecules X. Accordingly, in this exemplary embodiment, it is possible to achieve an increase in sensitivity of a sensor through the use of a spectroscopic method based on surface-enhanced Raman scattering.

In order to realize a high-sensitivity surface plasmons resonance sensor employing the surface-enhanced Raman scattering, it is preferable that the degree of enhancement of a local electric field (hereinafter, appropriately referred to as the degree of enhancement) be as large as possible. The degree of enhancement α is expressed by Expression (1) (M. Inoue, K. Ohtaka, J. Phys. Soc. Jpn., 52, 3853 (1983)). Here, αray represents the degree of enhancement at an excitation wavelength (which is equal to the Rayleigh scattering wavelength) and αram represents the degree of enhancement at a Raman scattering wavelength.

$$\alpha = \alpha ray \times \alpha ram \qquad (4)$$

Figure 5:
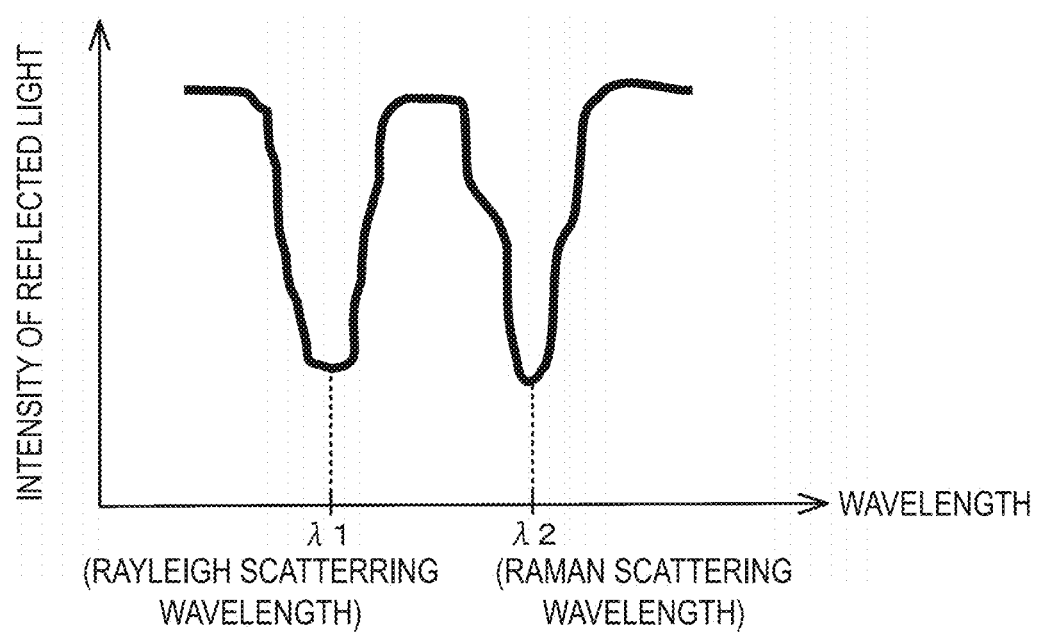
FIG. 5 is a characteristic diagram illustrating a Raman scattering spectroscopic method of generating two strong resonance peaks only in the vicinity of an excitation wavelength and a Raman scattering wavelength.

From Expression (4), in order to raise the degree of enhancement in the course of surface-enhanced Raman scattering, it is necessary to simultaneously raise the degree of enhancement in the course of excitation and the degree of enhancement in the course of Raman scattering. Accordingly, in this embodiment, two strong resonance peaks are generated only in the vicinity of the excitation wavelength and the Raman scattering wavelength, as shown in FIG. 5. As a result, it is possible to dramatically improve the enhancement effect of a local electric field through the synergy effect in both courses of scattering.

This exemplary embodiment is preferably based on the above-mentioned principle, but is not limited to the case where two resonance peaks are generated.

2. Optical Device

Figure 6A:
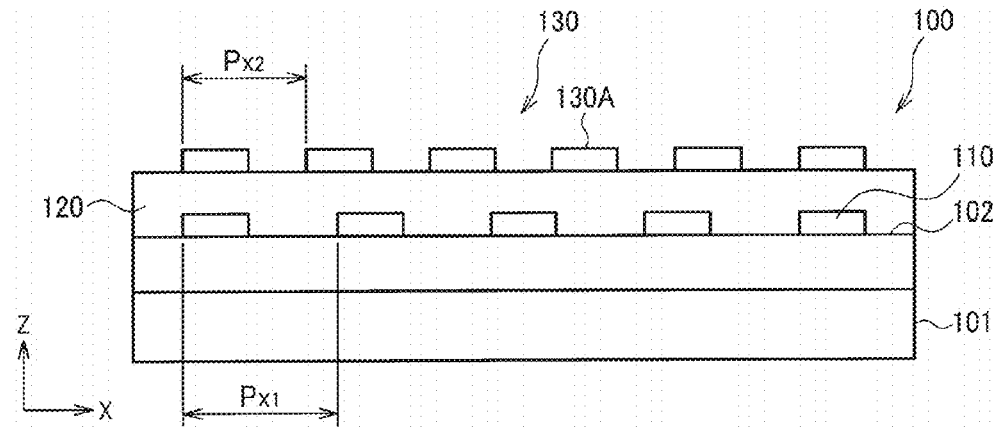
FIG. 6A is a partial cross-sectional view of an optical device and FIG. 6B is a partial plan view of the optical device.
Figure 6B:
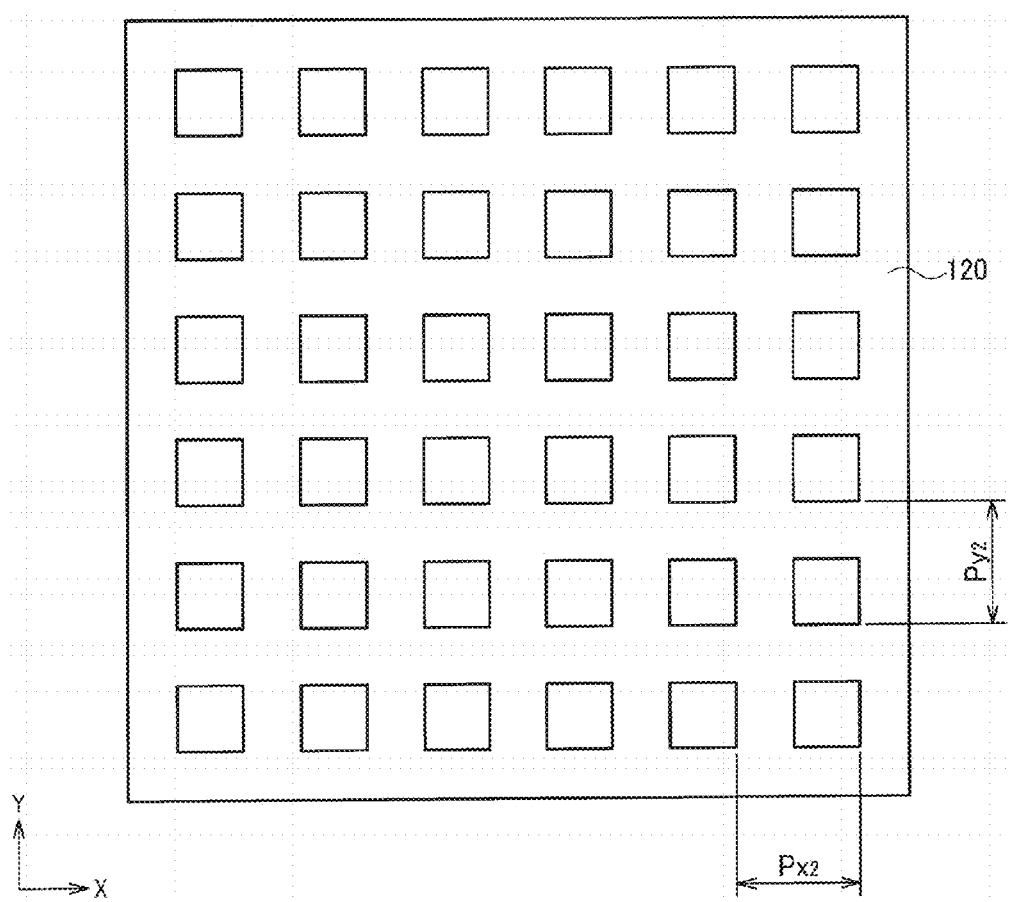
Figure 7A:
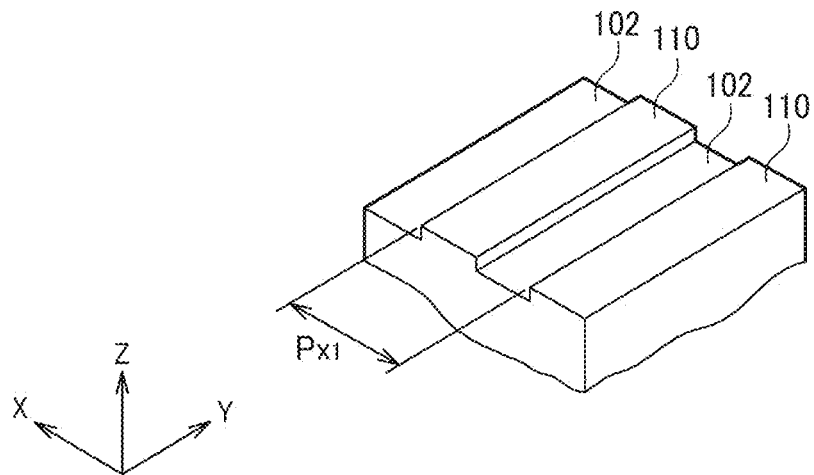
FIG. 7A is a perspective view illustrating a first protrusion group in a one-dimensional lattice structure and FIG. 7B is a perspective view illustrating a first protrusion group in a two-dimensional lattice structure.
Figure 7B:
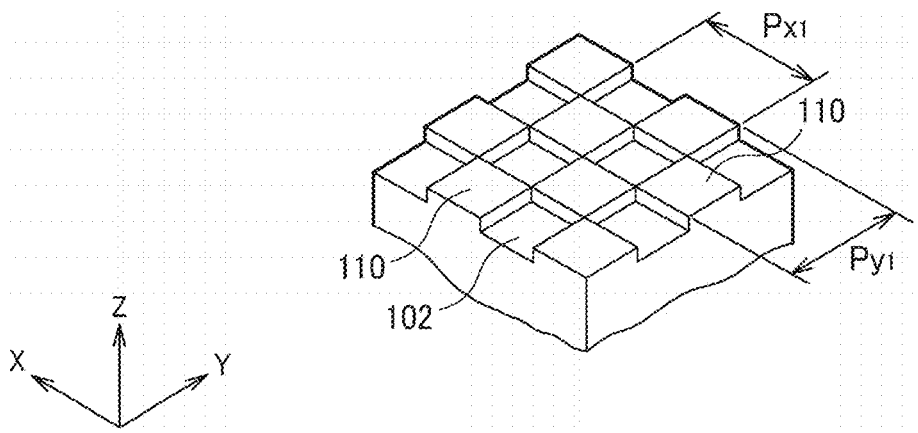

FIGS. 6A and 6B schematically illustrate the structure of a surface plasmons resonance sensor chip (optical device) 100 according to an exemplary embodiment of the invention. FIG. 6A is a cross-sectional view and illustrates a part of the sensor chip 100. FIGS. 7A and 7B are schematic perspective views of sensor chips in the course of manufacturing before forming a dielectric.

In the structure shown in FIGS. 6A and 6B, a metal nanostructure 130 (the second protrusion group) including metal nanoparticles 130A periodically arranged vertically and horizontally is superimposed on the surface of a first protrusion group 110 (see FIG. 7A) of a one-dimensional periodic metal lattice or a first protrusion group 110 (see FIG. 7B) of a two-dimensional periodic metal lattice with a dielectric layer 120 interposed therebetween.

A slight difference is provided between the periods of the first and second protrusion groups 110 and 130 and thus a kind of moire (interference fringe) having a large period. In this structure, by appropriately selecting the moire period, it is possible to strengthen the coupling of the localized surface plasmons LSP and the propagating surface plasmons PSP and thus to greatly enhance the local electric field appearing in the vicinity of the metal nanoparticles 130A.

As shown in FIG. 6A, the sensor chip 100 includes a base material (substrate) 101, a first protrusion group 110, a dielectric layer 120, and a second protrusion group (metal nanostructure) 130 including plural metal nanoparticles 130A.

Specifically, the base material 101 includes a metal surface (conductor surface in the broad sense) 102 of Ag (silver), Au (gold), or the like and is formed, for example, in a rectangular or circular flat plate shape. The base material 101 may be, for example, a substrate in which a metal thin film is formed on a glass substrate. As shown in FIG. 7A, in the first protrusion group 110, protrusions are one-dimensionally arranged with a first period Px1 in at least in a first direction X on the conductor surface 102 of the base material 101 and is formed of, for example, the same metal (conductor) as the conductor surface 102.

More specifically, the protrusions of the first protrusion group 110 are formed in a convex shape, which is convex from the conductor surface 102 of the base material 101, in a cross-section in the arrangement direction X of the protrusions. This convex shape is rectangular, trapezoidal, or circular. For example, as shown in FIG. 7A, the first protrusion group 110 may have a one-dimensional lattice structure formed in a striped shape parallel to a second direction Y perpendicular to (intersecting) the first direction X in the plan view of the base material 101. In this case, by using a linearly-polarized beam having a polarization direction in a direction perpendicular to grooves between the protrusions of the first protrusion group 110 as excitation light of a SP wave, it is possible to further enhance the degree of enhancement of an electric field.

Instead of the first protrusion group 110 shown in FIG. 7A, as shown in FIG. 7B, the protrusion group 110 may have a two-dimensional lattice structure in which protrusions are arranged with a first period Px1 in the first direction X and are arranged with a third period Py1 in the second direction Y in the plan view of the base material 101. In this case, by using a circularly-polarized beam as excitation light of a SP wave, it is possible to further enhance the degree of enhancement of an electric field.

The dielectric layer 120 formed of, for example, $SiO_2$ not absorbing the incident light is formed on the metal lattice including the conductor surface 102 and the first protrusion group 110 so as to cover the steps. The surface of the dielectric layer 120 is processed in a flat surface.

A metal nanostructure (the second protrusion group) 130 including plural metal nanoparticles 130A with a size and a height of 1 to several hundreds of nm, preferably 10 to 100 nm, and more preferably 20 to 60 nm is superimposed on the surfaces of the metal lattice 102 and 110 having periodicity with the dielectric layer 120 interposed therebetween.

In the metal nanostructure 130 shown in FIG. 6A, metal nanoparticles are arranged with the second period Px2 in the first direction X and are arranged with a fourth period Py2 in the second direction Y. Here, when the metal nanoparticles of the second protrusion group 130 are arranged with the second period Px2 in the first direction X similarly to the first protrusion group 110, the metal nanoparticles may not be arranged periodically in the second direction Y. By setting the constant period Px2 (Py2) to 50 to 1000 nm and preferably 500 nm or less, it is possible to raise the density of hot sites. In FIG. 6A, one convex portion is arranged at the right end of each of the first and second protrusion groups 110 and 130, but the relative position is not limited in the first and second protrusion groups 110 and 130.

Here, when the metal nanoparticles 130A arranged with a period smaller than the wavelength $\lambda$ of the incident light is irradiated with the incident light, the electric field of the incident light acts on free electrons present on the surface of the metal nanoparticles 130A to cause resonance. Accordingly, electrical dipoles due to the free electrons are excited in the metal nanoparticles 130A and an enhanced electric field stronger than the electric field of the incident light is formed. This is also called localized surface plasmons resonance (LSPR). This phenomenon is a phenomenon specific to an electrical conductor of the metal nanoparticles 130A with a size of 1 to several hundreds of nm which is smaller than the wavelength of the incident light.

3. Coupling of Localized Surface Plasmons LSP and Propagating Surface Plasmons PSP In this exemplary embodiment, when Px1>Px2 is established and the difference between the period Px1 and the period Px2 is small, it is possible to raise the density of hot sites by setting the second period of the second protrusion group 130 to any of Px1 and Px2. By setting the second period of the second protrusion group to Px2 (<Px1), it is possible to further raise the density of hot sites. Hereinafter, it is assumed that the period in the first direction X of the first protrusion group 110 is the first period Px1 and the period in the first direction X of the second protrusion group 130 is the second period Px2 (<Px1).

The reason of enhancement of the coupling of the localized surface plasmons LSP and the propagating surface plasmons PSP is considered as follows. It is thought that moire (interference fringe) having a necessary period Px is expressed by the difference between the first period Px1 and the second period Px2. The propagating surface plasmons PSP generated in the interface between the first protrusion group 110 and the dielectric layer 120 is coupled to an evanescent field having a wave number of K0. The wave number K0 is determined by the moire period Px and is $2\pi/Px$. It is thought that the presence of the moire enhances the coupling of the localized surface plasmons LSP and the propagating surface plasmons PSP and thus a large enhanced electric field appears. The moire period Px in the first direction X is expressed by Expression (1).

$$Px = Px1 \cdot Px2 / (Px1 - Px2) \qquad (1)$$

On the basis of $\lambda$>Px1>Px2 and Expression (1), the following expression is obtained.

$$Px1 - Px2 = Px1 - [Px/(Px + Px1)]Px1$$
$$= Px1[1 - Px/(Px + Px1)]$$
$$= Px1[1 - 1/(1 + Px1/Px)]$$

Here, because of 0<Px1<Px, Expression (2) is established.

$$0 < Px1 - Px2 < Px1/2 \quad (2)$$

When the wave number of the propagating surface plasmons PSP is defined as K0, Expression (3) is established from Expression (1).

$$Px = 2\pi/K0 = Px1*Px2/(Px1-Px2) \quad (3)$$

In this way, it can be seen that the wave number of the propagating surface plasmons PSP is not determined by only the second period Px2 of the second protrusion group 130 as a hot site as described in "Experimental Study of the Interaction between Localized and Propagating Surface Plasmons", OPTICS LETTERS/Vol. 34, No. 3/Feb. 1, 2009, but is determined by the difference and the product of the first and second periods Px1 and Px2 as expressed by Expression (3). Accordingly, the period Px2 of the second protrusion group 130 in which the localized surface plasmons LSP is excited does not have to be set to be large as described in "Experimental Study of the Interaction between Localized and Propagating Surface Plasmons", OPTICS LETTERS/Vol. 34, No. 3/Feb. 1, 2009, but it is possible to raise the sensitivity of the sensor chip 100 by raising the density of the second protrusion group 130 as a hot site.

When the first protrusion group 110 has the structure shown in FIG. 7B, Expressions 1 to 3 and λ>Py>Py1>Py2 are established in the second direction Y by replacing Px, Px1, and px2 of Expressions 1 to 3 with Py (the moire period in the Y direction), Py1, and Py2 respectively.

Figure 3:
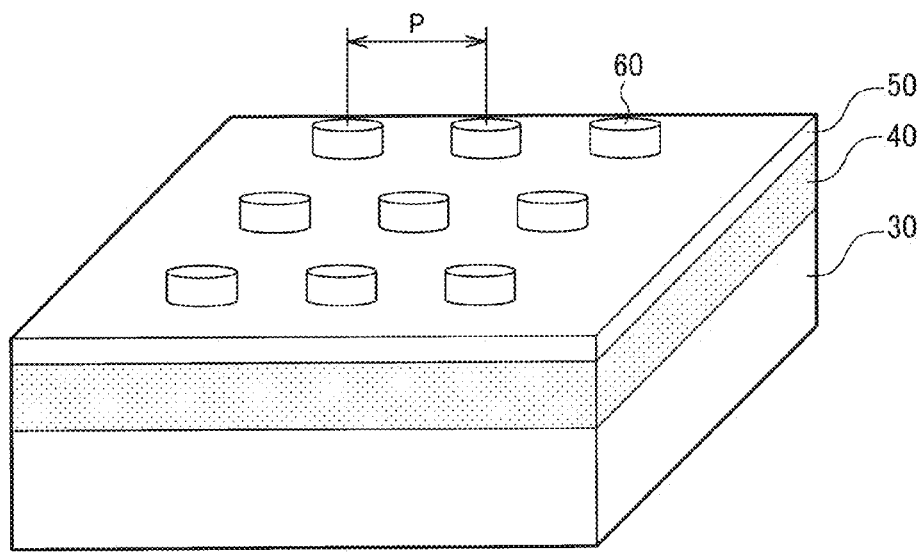
FIG. 3 is a diagram illustrating a sensor using propagating surface plasmons and localized surface plasmons according to the related art.
Figure 8:
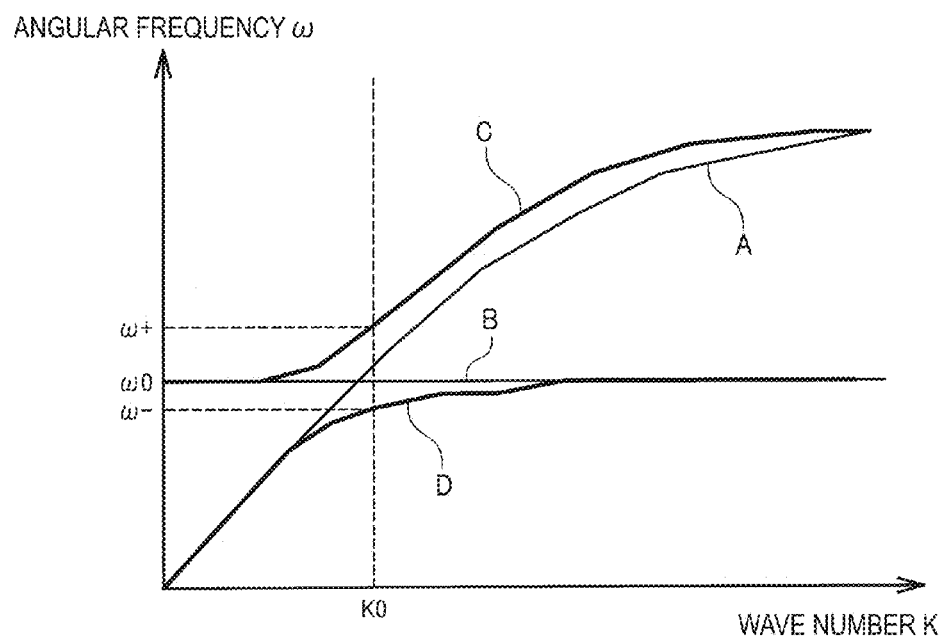
FIG. 8 is a characteristic diagram illustrating a dispersion curve of the localized surface plasmons and the propagating surface plasmon.

FIG. 8 shows the dispersion relationship between the localized surface plasmons LSP and the propagating surface plasmons PSP in the sensor chip 100. In FIG. 8, A presents the dispersion curve of the propagating surface plasmons PSP and B represents the dispersion curve of the localized surface plasmons LSP. When LSP and PSP are coupled, two dispersion curves are separated from each other at the intersection of the curves A and B and in the vicinity thereof and curves C and D are the corresponding dispersion curves. When the excitation wavelength is defined as λ (which corresponds to the angular frequency ω0 in FIG. 8), the propagating surface plasmons PSP and the localized surface plasmons LSP are strongly coupled to each other and thus a large local electric field appears, under the condition (for example, which corresponds to the wave number K0 in FIG. 3) that the moire period P is the intersection of A and B or the vicinity thereof. Accordingly, Px1 and Px2 are determined to satisfy Expression (3). Here, Px<λ is satisfied. There are plural combinations of Px1 and Px2 satisfying both Expression (3) and λ>Px>Px1>Px2, and the optimal combination can be selected therefrom.

In FIG. 8, the straight line extending upward from the wave number K0 intersects the dispersion curves C and D and a large local electric field appears in the two intersections, that is, at the resonance wavelengths ω+ and ω−. Therefore, the period Px2 of the metal nanoparticles 130A in the second protrusion group 130 may be determined and the period Px1 of the first protrusion group 110 in Expression (3) may be determined, so that the resonance wavelength ω− matches the excitation wavelength and the resonance wavelength ω+ matches the Raman scattering wavelength.

4. Verification of Specific Example and Advantages

Figure 9:
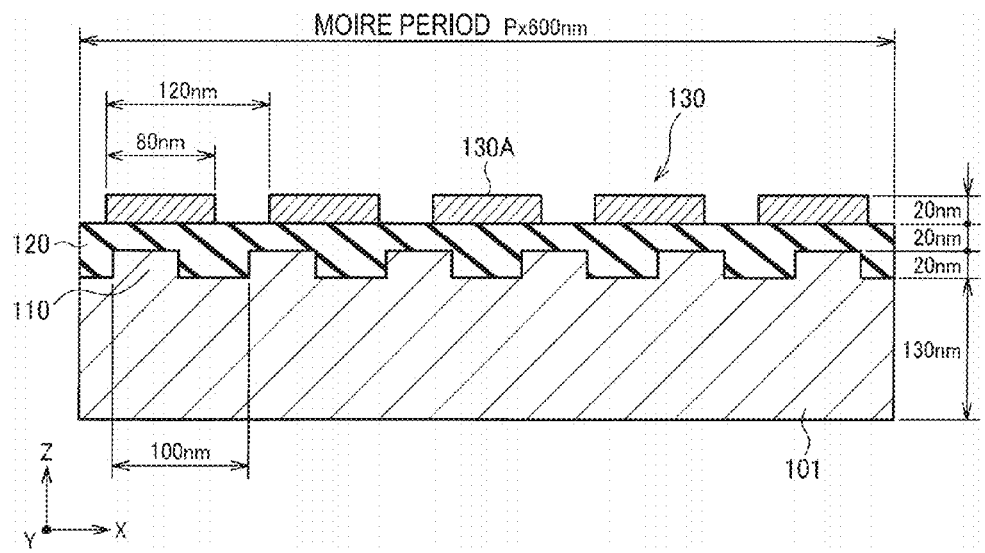
FIG. 9 is a cross-sectional view of an example of the optical device.

A more specific example is shown in FIG. 9. The Ag nanoparticles 130A having a columnar shape are arranged with the second period Px2=the fourth period Py2=120 nm in the first and second directions X and Y. The length of one side of the Ag nanoparticle 130A is 80 nm and the height thereof is 20 nm. On the other hand, the Au lattice 110 is one-dimensional, the first period Px1 is 100 nm, and the height is 20 nm. The Ag nanoparticles 130A are formed on the Au lattice 110 with the SiO$_2$ layer 120 interposed therebetween. The thickness of the SiO$_2$ layer 120 is 40 nm in a thick place and 20 nm in a thin place. The moire period caused by these two periodic structures is 600 nm in Expression (1). FIG. 9 shows the structure of a length portion corresponding to one period of the moire.

Figure 10A:
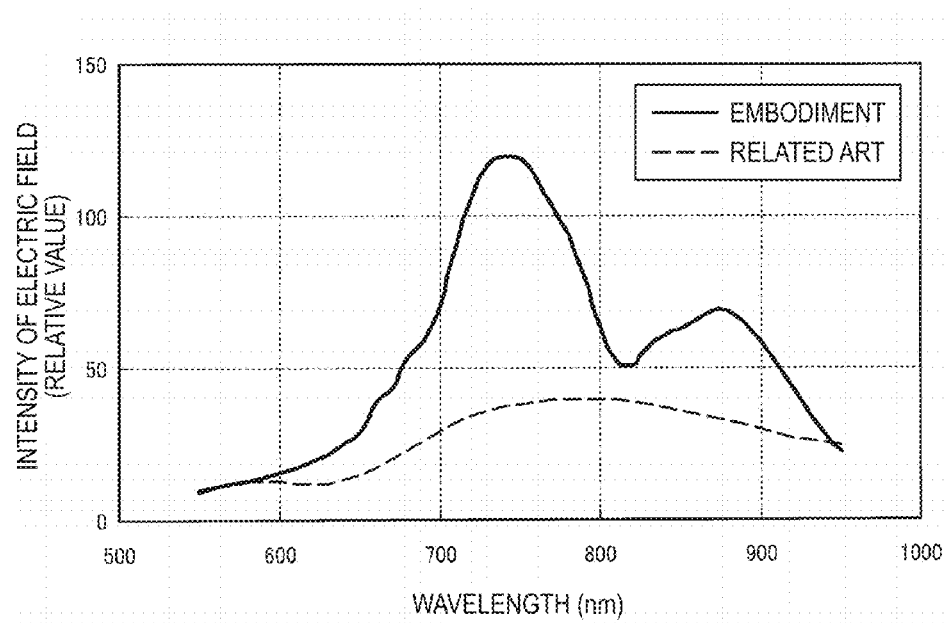
FIGS. 10A and 10B are characteristic diagrams illustrating analysis of an X component and the relationship between the magnitude of a local electric field and an optical wavelength with respect to the X component.
Figure 10B:
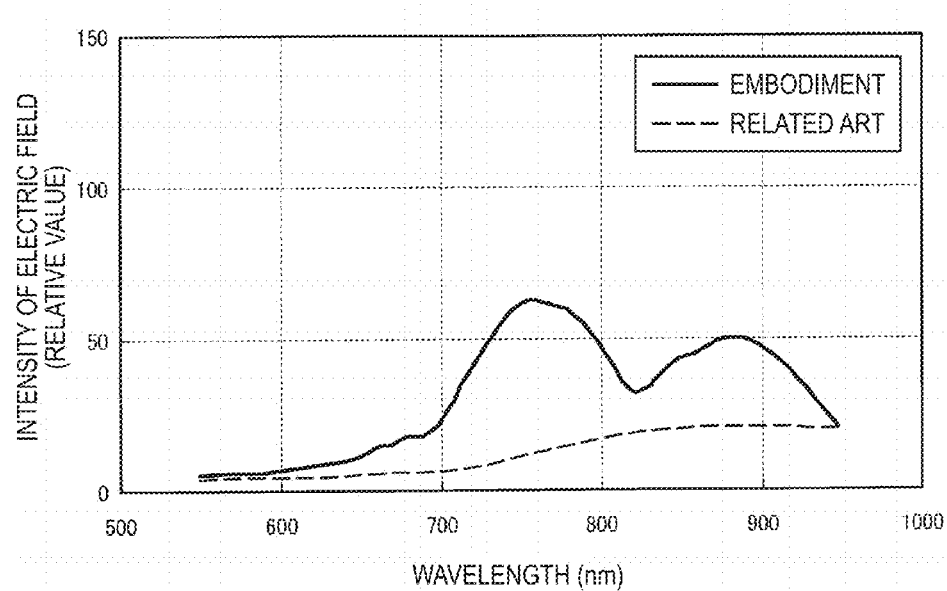

FIGS. 10A and 10B show the relationship between the magnitude of the local electric field acquired through analysis of a finite difference time domain (FDTD) method and the wavelength of light. FIG. 10A shows the X component of the local electric field and FIG. 10B shows the Z component of the local electric field. The characteristic of the example shown in FIG. 9 is marked by a solid line and the characteristic of the related art ("Experimental Study of the Interaction between Localized and Propagating Surface Plasmons", OPTICS LETTERS/Vol. 34, No. 3/Feb. 1, 2009) for comparison is marked by a broken line. In FIGS. 10A and 10B, it can be seen that the enhanced electric field appearing in the fine metal structure of the example is larger substantially three times in the X component and is larger substantially four times in the Z component than the enhanced electric field shown in the fine metal structure of the related art.

In FIGS. 10A and 10B, double-humped resonance peaks clearly appear at a wavelength of 740 nm and a wavelength of 870 nm in the characteristics of the fine metal structure of the example. This means that the local surface plasmons LSP and the propagating surface plasmons PSP are strongly coupled and thus an enhanced electric field much larger than that of the fine metal structure of the related art due to this coupling appears. On the other hand, the double-humped resonance peaks are not recognized from the characteristics of the fine metal structure of the related art. The reason is that the period of the structure of the related art is 120 nm which is short and is farther separated from the period condition (substantially 600 nm more or less) in which the localized surface plasmons LSP and the propagating surface plasmons PSP are strongly coupled.

Figure 11A:
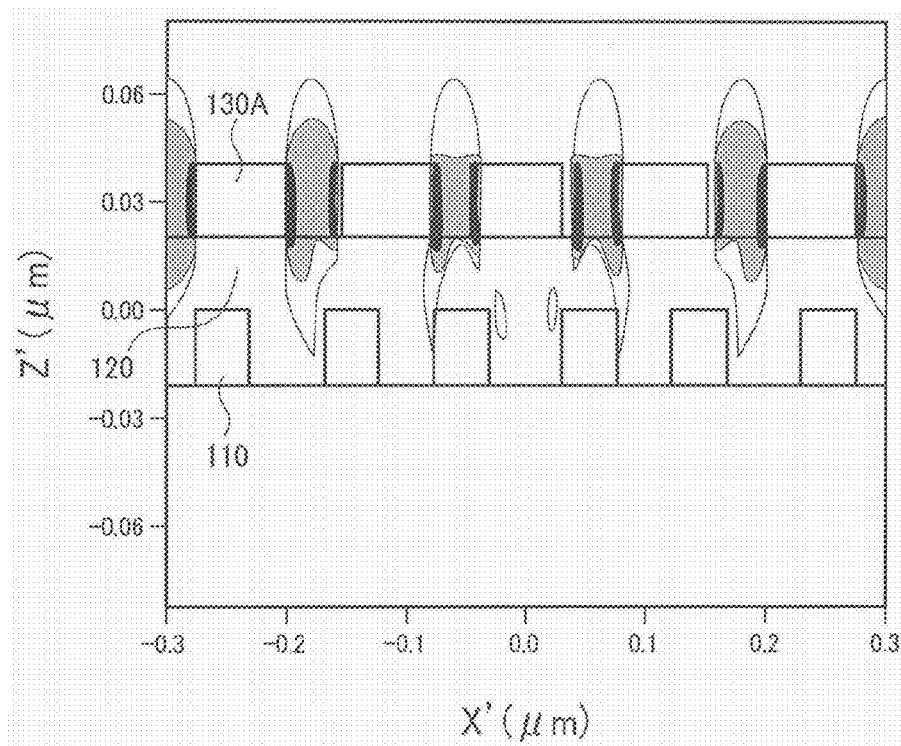
FIGS. 11A and 11B are characteristic diagrams illustrating analysis of an X component and a distribution of a local electric field with respect to the X component.
Figure 11B:
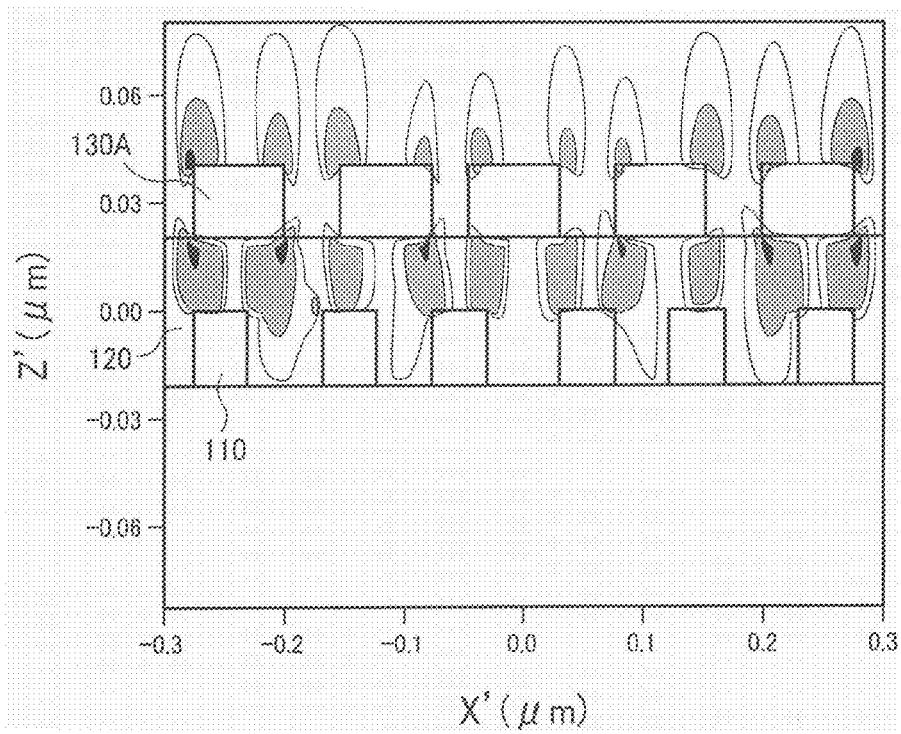

FIGS. 11A and 11B show an example of a local electric field distribution appearing in the example (see FIG. 9). This distribution is calculated through the FDTD method. In FIGS. 11A and 11B, the horizontal width of the calculation area is 600 nm which is equal to one period of the moire. In one period of the moire, five Ag nanoparticles 130A having a columnar shape are arranged with a gap of 120 nm. The Au lattice 110 is disposed under the Ag nanoparticles with the SiO$_2$ layer (dielectric layer) 120 interposed therebetween. The period of the Au lattice 110 is 100 nm and the structure corresponding to six periods are shown in FIGS. 11A and 11B. When a linearly-polarized beam (of which the polarization direction is the X direction) of a wavelength of 740 nm is vertically incident on the structure from the upside, a large local electric field appears in the vicinity of the Ag nanoparticles 130A. FIG. 11A shows the X component of the local electric field and a large local electric field appears in the gaps between the five Ag nanoparticles 130A and the vicinities thereof. FIG. 11B shows the Z component of the local electric field and a large local electric field appears on the top of the five Ag nanoparticles 130A and the vicinities thereof. A large local electric field appears under the Ag nanoparticles 130A, but it is difficult to use for sensing. The number of hot sites per period is substantially 5×5=25 times that of the structure shown in "Experimental Study of the Interaction between Localized and Propagating Surface Plasmons", OPTICS LETTERS/Vol. 34, No. 3/Feb. 1, 2009. The magnitude of the enhanced electric field between the hot sites is sufficiently uniform in practice.

In order to implement a high-sensitivity surface plasmons resonance sensor employing the surface plasmons resonance SPR, the degree of enhancement of the local electric field is preferably as large as possible. As described in the related art document J. Phys. Soc. Jpn. 52, 3853 (1983), the degree of enhancement α is expressed by Expression (5).

α=(degree of enhancement at excitation wavelength)× (degree of enhancement at Raman scattering wavelength)    (5)

As can be seen from Expression (5), in order to raise the degree of enhancement in the Raman scattering, it is necessary to raise both the degree of enhancement in the course of excitation and the degree of enhancement in the course of scattering. Accordingly, when the sensor chip 100 has strong resonance peaks at the excitation wavelength and in the vicinity of the scattering wavelength, the enhancement effect is drastically improved due to the synergy effect of both courses.

In this example, as shown in FIGS. 10A and 10B, the peaks of the enhanced electric field are recognized at the wavelength of 740 nm and the wavelength of 870 nm (these two resonance wavelengths correspond to ω+ and ω− in FIG. 8). Therefore, when the fine metal structure is used in the SPR sensor, it is preferable that the excitation wavelength match the vicinity of 740 nm and the scattering wavelength match the vicinity of 870 nm. Accordingly, a large electric field enhancement effect due to the surface plasmons resonance SPR can be expected. According to the definition of the degree of enhancement of an electric field expressed by Expression (5), at least the degree of enhancement of $10^8$ times can be expected. When the difference (Raman shift) between the excitation wavelength and the scattering wavelength is small, the excitation wavelength and the scattering wavelength may match the vicinity of only one resonance peak.

When it is intended to match the excitation wavelength and the scattering wavelength with the two resonance peaks, the structural parameters of the metal nanoparticles 130A and the metal lattice 110 can be selected and then the moire period P (Px and Py) can be determined. The scattering wavelength, that is, the Raman shift, differs depending on the detection target molecules.

5. Manufacturing Method

Figure 12A:
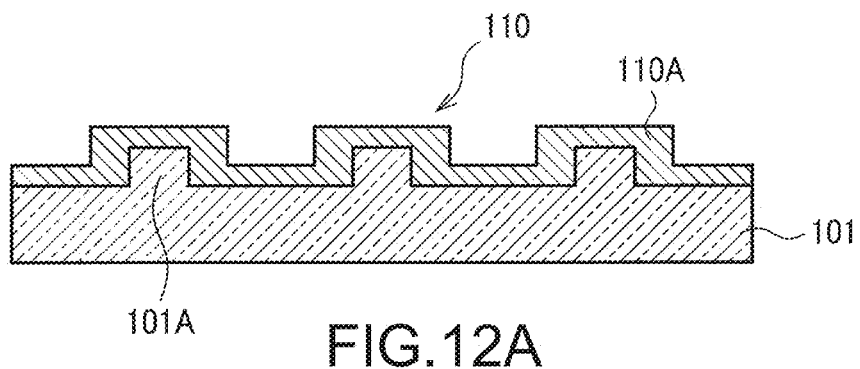
FIGS. 12A to 12D are diagrams illustrating a manufacturing process.
Figure 12B:
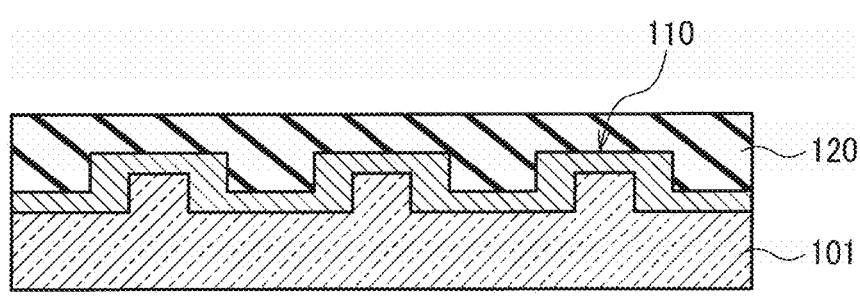
Figure 12C:
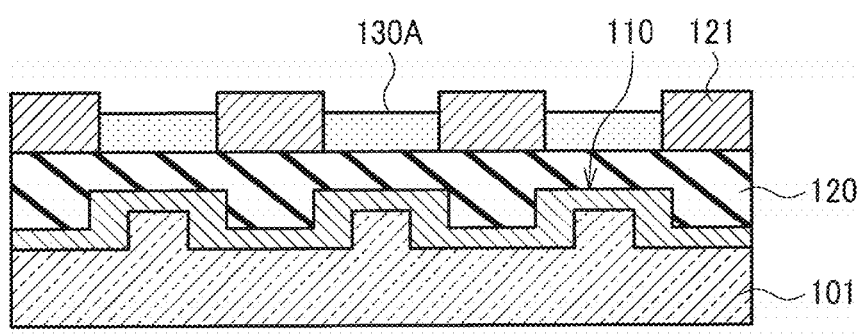
Figure 12D:
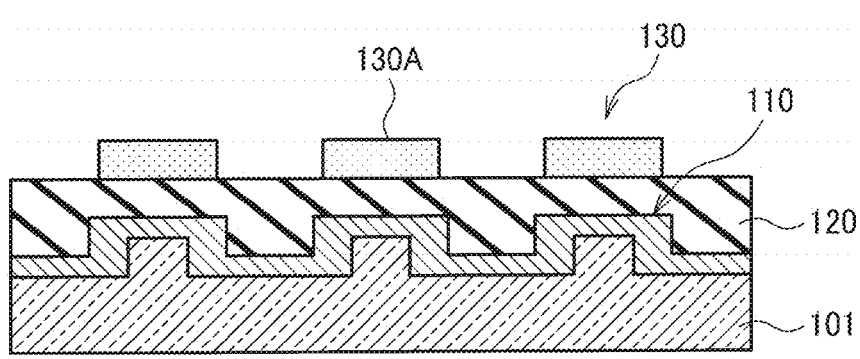
Figure 13A:
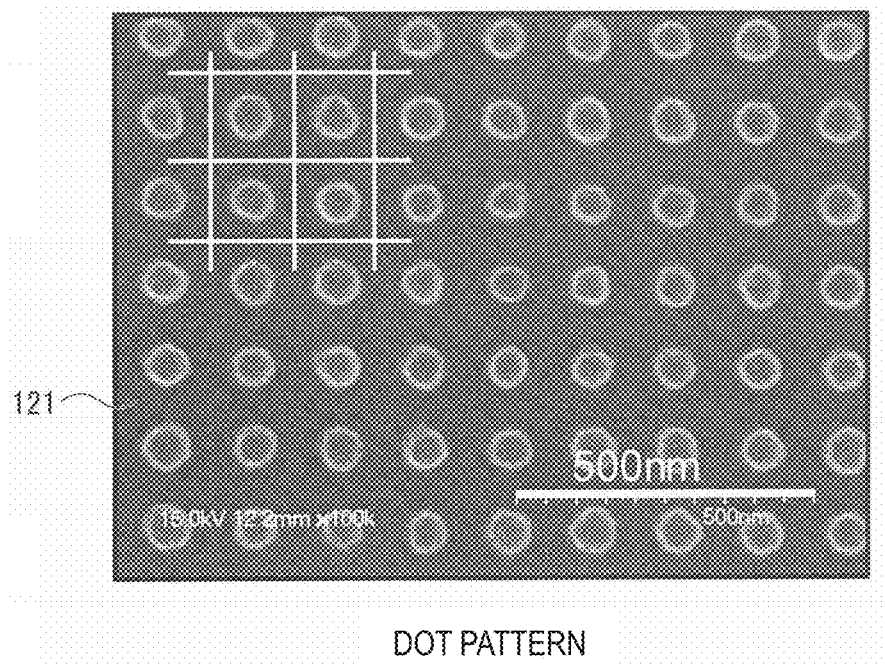
FIGS. 13A and 13B are diagrams illustrating examples of a resist pattern.
Figure 13B:
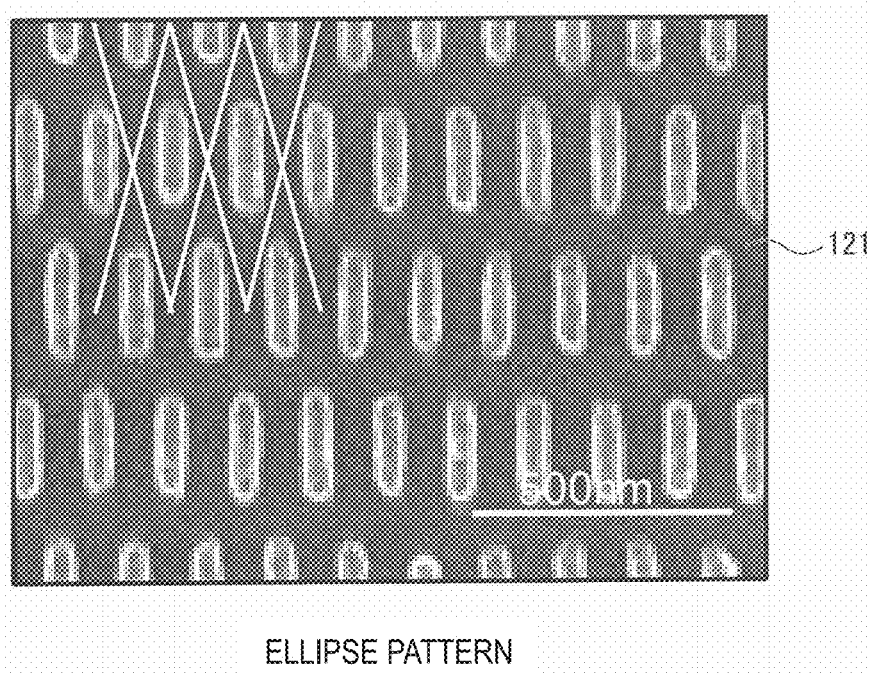

FIGS. 12A to 12D show the method of manufacturing the sensor chip 100 according to the example shown in FIG. 9. First, as shown in FIG. 12A, an uneven lattice 101A is formed on the surface of a quartz glass substrate 101 through a photolithographic method or the like. Then, as shown in FIG. 12A, an Au film 110A is formed with a thickness of 100 nm on the surface of the uneven lattice 101A through the use of a sputtering method and an Au lattice (first protrusion group) 110 is formed. Then, as shown in FIG. 12B, an $SiO_2$ layer (dielectric layer) 120 is formed on the Au lattice 110 through the use of a sol-gel method to flatten the surface of the $SiO_2$ layer 120. As shown in FIG. 12C, a resist pattern 121 is formed on the surface of the flattened $SiO_2$ layer 120 through the use of an imprinting method or the like. As the resist pattern 121, an example of a dot pattern is shown in FIG. 13A and an example of an elliptical pattern is shown in FIG. 13B. Then, as shown in FIG. 12C, by depositing Ag on the resist pattern 121 in vacuum and then removing the resist pattern 121, a metal nanostructure (second protrusion group) 130 in which Ag nanoparticles 130A are two-dimensionally arranged is formed (lift-off) as shown in FIG. 12D. In this example, the material of the metal nanostructure (second protrusion group) 130 and the material of the metal lattice structure 110 are different metals, but a combination of the same metals (for example, Ag and Ag or Au and Au) may be used.

6. Detection Apparatus

Figure 14:
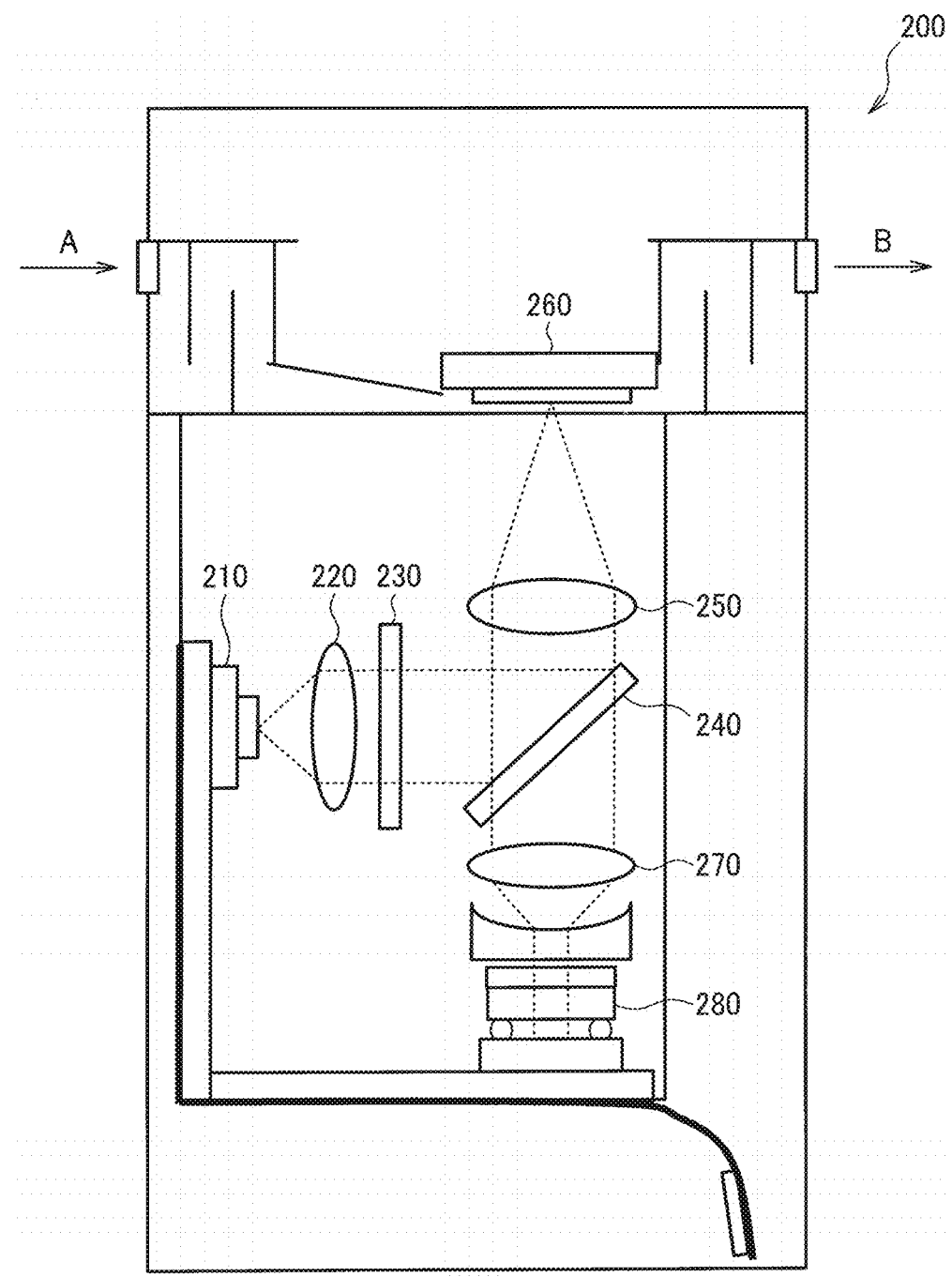
FIG. 14 is a diagram schematically illustrating a detection apparatus.

FIG. 14 is a schematic diagram illustrating an example of a detection apparatus 200 including the above-mentioned sensor chip (optical device) 100 (referenced by reference numeral 260 in FIG. 14). A target material (not shown) is input to the detection apparatus 200 from the A direction and is output in the B direction therefrom. A laser beam emitted from an excitation light source 210 becomes a parallel beam through a collimator lens, passes through a polarization control element 230, and is guided toward the sensor chip 260 through a dichroic mirror 240. The laser beam is focused by an objective lens 250 and is incident on the sensor chip 260. At this time, the target material (not shown) is disposed on the surface (for example, the surface on which the metal nanostructure 130 is formed) of the sensor chip 260. By controlling the driving of a fan (not shown), the target material is introduced into a transport unit through an input port and is output from the transport unit through an output port.

When a laser beam is incident on the surface of the sensor chip 260, a very strong enhanced electric field is generated in the vicinity of the metal nanostructure 130 by the surface plasmons resonance SPR. When one or several target particles enter the enhanced electric field, a Raman scattered light beam is generated therefrom. The Raman scattered light beam passes through the objective lens 250, is guided toward an optical detector 280 through the dichroic mirror 240, is focused by a focusing lens 270, and is incident on the optical detector (for example, a diffraction grating type spectroscope) 280. Then, the light beam is decomposed in spectrum by the optical detector 280 and spectrum information shown in FIG. 4B can be obtained. According to this configuration, since the detection apparatus includes the sensor chip 100, the sensitivity of the sensor is improved and it is thus possible to specify the target material from the Raman scattering spectrum.

While the exemplary embodiments of the invention have been described above in detail, it should be easily understood by those skilled in the art that the invention can be modified in various forms without substantially departing from the novel details and advantages of the invention. Accordingly, all the modified examples belong to the scope of the invention.

The entire disclosure of Japanese Patent Application No. 2011-227746, filed Oct. 17, 2011, is expressly incorporated by reference herein.

What is claimed is:

1. A detection apparatus comprising:
   a light source;
   an optical device that emits light specific to a sample by introduction of the sample and irradiation with light of a wavelength λ from the light source; and
   an optical detection unit that detects the light specific to the sample emitted from the optical device,
   wherein the optical device includes
      a first protrusion group in which protrusions protruding from a conductor surface of a substrate are arranged in a first direction with a first period, a dielectric layer that covers the conductor surface and the first protrusion group, and a second protrusion group in which metal nanoparticles are arranged on the dielectric layer in the first direction with a second period different from the first period, and wherein any of a combination in which the first period is Px1 and the second period is Px2 and a combination in which the first period is Px2 and the second period is Px1 satisfies λ>Px1>Px2 and 0<Px1−Px2<Px1/2.

2. The detection apparatus according to claim 1, wherein the second period of the second protrusion group is set to Px2 and the first period of the first protrusion group is set to Px1.

3. The detection apparatus according to claim 1, wherein moire with a period Px is formed in the first direction on the basis of the difference and the product of the first period and the second period and the period Px of the moire satisfies λ>Px>Px1>Px2.

4. The detection apparatus according to claim 1, wherein the first protrusion group is a metal lattice in which the protrusions are arranged in the first direction with the first period, and wherein the second protrusion group is a metal nanostructure in which the metal nanoparticles are arranged in the first direction with the second period and are periodically arranged in a second direction intersecting the first direction.

5. The detection apparatus according to claim 1, wherein the first protrusion group is a two-dimensional metal lattice in which the protrusions are arranged in the first direction with the first period and are arranged in a second direction intersecting the first direction with a third period, wherein the second protrusion group is a metal nanostructure in which the metal nanoparticles are arranged in the first direction with the second period and are arranged in the second direction with a fourth period, and wherein any of a combination in which the third period is Py1 and the first period is Py2, a combination in which the third period is Py1 and the second period is Py2, a combination in which the fourth period is Py1 and the first period is Py2, and a combination in which the fourth period is Py1 and the second period is Py2 satisfies λ>Py2>Py1 and 0<Py2−Py1<Py2/2.

6. The detection apparatus according to claim 1, wherein the surface of the dielectric layer on which the second protrusion group is formed is a flat surface.

7. A detection apparatus comprising:
a light source;
an optical device that emits light specific to a sample by introduction of the sample and irradiation with light from the light source; and
an optical detection unit that detects the light specific to the sample emitted from the optical device,
wherein the optical device includes
a first protrusion group in which protrusions protruding from a conductor surface of a substrate are arranged in a first direction with a first period,
a dielectric layer that covers the conductor surface and the first protrusion group, and
a second protrusion group in which metal nanoparticles are arranged on the dielectric layer in the first direction with a second period different from the first period, and wherein moire has a period that is based on a difference between the first period and the second period and is expressed to enhance the coupling of local surface plasmons and propagating surface plasmons through the use of the moire.

8. An optical device comprising:
a first protrusion group in which protrusions protruding from a conductor surface of a substrate are arranged in a first direction with a first period;
a dielectric layer that covers the conductor surface and the first protrusion group; and
a second protrusion group in which metal nanoparticles are arranged on the dielectric layer in the first direction with a second period different from the first period, and
wherein any of a combination in which the first period is Px1 and the second period is Px2 and a combination in which the first period is Px2 and the second period is Px1 satisfies λ>Px1>Px2 and 0<Px1−Px2<Px1/2, where λ represents the wavelength of irradiation light.

9. The optical device according to claim 8, wherein the second period of the second protrusion group is set to Px2 and the first period of the first protrusion group is set to Px1.

10. The optical device according to claim 8, wherein moire with a period Px is formed in the first direction on the basis of the difference and the product of the first period and the second period and the period Px of the moire satisfies λ>Px>Px1>Px2.

11. The optical device according to claim 8, wherein the first protrusion group is a metal lattice in which the protrusions are arranged in the first direction with the first period, and wherein the second protrusion group is a metal nanostructure in which the metal nanoparticles are arranged in the first direction with the second period and are periodically arranged in a second direction intersecting the first direction.

12. The optical device according to claim 8, wherein the first protrusion group is a two-dimensional metal lattice in which the protrusions are arranged in the first direction with the first period and are arranged in a second direction intersecting the first direction with a third period, wherein the second protrusion group is a metal nanostructure in which the metal nanoparticles are arranged in the first direction with the second period and are arranged in the second direction with a fourth period, and wherein any of a combination in which the third period is Py1 and the first period is Py2, a combination in which the third period is Py1 and the second period is Py2, a combination in which the fourth period is Py1 and the first period is Py2, and a combination in which the fourth period is Py1 and the second period is Py2 satisfies λ>Py2>Py1 and 0<Py2−Py1<Py2/2.

13. The optical device according to claim 8, wherein the surface of the dielectric layer on which the second protrusion group is formed is a flat surface.

* * * * *